US008118595B2

(12) United States Patent
Discko, Jr. et al.

(10) Patent No.: US 8,118,595 B2
(45) Date of Patent: Feb. 21, 2012

(54) CONFORMING GINGIVA RETRACTION COMPRESSION CAP AND METHOD OF RETRACTING TISSUE AROUND A TOOTH

(75) Inventors: John J. Discko, Jr., Trumbull, CT (US); William B. Dragan, Easton, CT (US)

(73) Assignee: Centrix, Inc., Shelton, CT (US)

( * ) Notice: Subject to any disclaimer, the term of this patent is extended or adjusted under 35 U.S.C. 154(b) by 0 days.

(21) Appl. No.: 12/291,648

(22) Filed: Nov. 12, 2008

(65) Prior Publication Data

US 2009/0075240 A1 Mar. 19, 2009

Related U.S. Application Data

(63) Continuation-in-part of application No. 11/825,802, filed on Jul. 9, 2007, which is a continuation-in-part of application No. PCT/US2007/008232, filed on Mar. 30, 2007, which is a continuation-in-part of application No. 11/398,134, filed on Apr. 5, 2006, now Pat. No. 7,241,143.

(51) Int. Cl.
*A61C 5/14* (2006.01)

(52) U.S. Cl. ........................................ 433/136

(58) Field of Classification Search .................... 433/34, 433/37, 38, 39, 136, 214
See application file for complete search history.

(56) References Cited

U.S. PATENT DOCUMENTS

| | | | |
|---|---|---|---|
| 2,396,203 A | 3/1946 | Robinson | |
| 2,620,502 A | 12/1952 | Russak | |
| 3,056,205 A | 10/1962 | Ennor | |
| 3,238,620 A | 3/1966 | Robertson | |
| 3,380,446 A | 4/1968 | Martin | |
| 3,471,058 A | 10/1969 | Latham et al. | |
| 3,548,500 A | 12/1970 | Cohen | |
| 3,705,585 A | 12/1972 | Saffro | 128/303.1 |
| 4,071,955 A | 2/1978 | Julius | 32/34 |
| 4,144,882 A | 3/1979 | Takemoto et al. | 128/172.1 |
| 4,173,219 A | 11/1979 | Lentine | 128/260 |
| 4,348,178 A | 9/1982 | Kurz | 433/6 |
| 4,372,314 A | 2/1983 | Wall | 128/296 |
| 4,465,462 A * | 8/1984 | Ticknor | 433/136 |
| 4,468,202 A | 8/1984 | Cohen | 433/199 |
| 4,531,914 A | 7/1985 | Spinello | 433/136 |
| 4,543,063 A | 9/1985 | Cohen | 433/175 |
| 4,551,100 A | 11/1985 | Fischer | 433/218 |
| 4,617,950 A | 10/1986 | Porteous et al. | 132/91 |
| 4,677,139 A | 6/1987 | Feinmann | 523/111 |
| 4,867,680 A | 9/1989 | Hare et al. | 433/37 |
| 4,961,706 A | 10/1990 | Jefferies | 433/39 |
| 5,146,940 A | 9/1992 | Hamada | 135/34.2 |
| 5,190,457 A | 3/1993 | Schreinemakers | 433/214 |
| 5,213,498 A | 5/1993 | Pelerin | 433/37 |
| 5,362,495 A | 11/1994 | Lesage | 424/435 |

(Continued)

*Primary Examiner* — Cris L Rodriguez
*Assistant Examiner* — Eric Rosen
(74) *Attorney, Agent, or Firm* — Fattibene and Fattibene LLC; Paul A. Fattibene

(57) ABSTRACT

A rolled compression cap having a central bore. The rolled compression cap has adjacent layers that slide or telescope to conform to the prepared tooth and to apply more direct mechanical pressure to the interface between the prepared tooth and the gingiva. The gingiva or gum retracts from the tooth forming or widening a gingival sulcus. This improves the preparation of the tooth for taking an impression and fitting a crown or cap. In one embodiment, a rolled compression cap is pre-dosed or soaked with an astringent material or retraction agent. In another embodiment, the central bore of the rolled compression cap is filled with a paste-like or gel material containing an astringent or hemostatic agent.

20 Claims, 4 Drawing Sheets

U.S. PATENT DOCUMENTS

| | | | |
|---|---|---|---|
| 5,385,469 A | 1/1995 | Weissman | 433/40 |
| 5,480,303 A | 1/1996 | Groth | 433/136 |
| 5,639,445 A | 6/1997 | Curtis et al. | 424/49 |
| 5,676,543 A | 10/1997 | Dragan | 433/136 |
| 5,955,513 A | 9/1999 | Hare | 523/109 |
| 5,980,249 A | 11/1999 | Fontenot | 433/80 |
| 6,050,821 A | 4/2000 | Klaassen et al. | 433/214 |
| 6,155,262 A | 12/2000 | Thornton et al. | 128/859 |
| 6,375,461 B1 * | 4/2002 | Jensen et al. | 433/136 |
| 6,890,177 B2 | 5/2005 | Dragan | 433/136 |
| 7,189,075 B2 | 3/2007 | Dragan | 433/136 |
| 7,195,483 B2 | 3/2007 | Dragan | 433/136 |
| 7,241,143 B2 | 7/2007 | Dragan | 433/136 |
| 2003/0228339 A1 | 12/2003 | El-Nokaly et al. | 424/401 |
| 2004/0126740 A1 | 7/2004 | Coopersmith | 433/136 |
| 2004/0234926 A1 | 11/2004 | Halldin et al. | 433/173 |
| 2004/0265777 A1 | 12/2004 | Heasley | 433/136 |
| 2005/0069838 A1 | 3/2005 | Kollefrath et al. | 433/136 |
| 2005/0118552 A1 | 6/2005 | Coopersmith | 433/136 |
| 2005/0202367 A1 * | 9/2005 | Kollefrath et al. | 433/136 |
| 2006/0063128 A1 | 3/2006 | Dragan | 433/89 |
| 2007/0128581 A1 | 6/2007 | Dustan-Maher | 433/217.1 |
| 2007/0259313 A1 | 11/2007 | Dragan et al. | 433/136 |

* cited by examiner

CONFORMING GINGIVA RETRACTION COMPRESSION CAP AND METHOD OF RETRACTING TISSUE AROUND A TOOTH

RELATED APPLICATIONS

This application is a continuation in part of application Ser. No. 11/825,802 filed Jul. 9, 2007 which is a continuation in part of International Application No. PCT/US07/08232 filed Mar. 30, 2007, which is a continuation in part of application Ser. No. 11/398,134 filed Apr. 5, 2006, now U.S. Pat. No. 7,241,143, all of which are herein incorporated by reference in their entirety.

FIELD OF THE INVENTION

This invention is directed to a method and device for effecting retraction of tissue, and more specifically to a compression cap placed over a prepared tooth for retracting the gum or gingiva forming a gingival sulcus.

BACKGROUND OF THE INVENTION

The traditional method for retracting gingival tissue prior to the taking of an impression of a prepared tooth to form a crown or bridge is to mechanically pack a small length of cord saturated with or without an astringent about the base of the tooth to enlarge the gingival sulcus or space about the base of a tooth. After a period of time, the cord is removed from the enlarged space defined about the base of the tooth. Upon the removal of the cord, it frequently happens that coagulum formed to stop the bleeding or seepage of fluid is removed with the cord to result in the seepage of additional bleeding into the space. As a result, an impression cannot be made of the prepared tooth until the additional bleeding can be controlled or stopped. Thus, the traditional procedure for enlarging the space between the gum and the base of the tooth necessary for taking an accurate impression is tedious, time consuming, and painful or extremely uncomfortable for the patient. Also, there exists the danger that the dentist may accidentally force the cord beyond the physiologic limit of the space to create a potential periodontal pocket which can cause the tooth to eventually be lost. The general practice of using the cord technique is relatively difficult and tedious for the dentist.

In the event that the space between the tooth and the gum that has to be retracted is very small, it becomes even more difficult for the dentist to place the cord without injuring the gum tissue and from forcing the cord beyond the physiologic limit, rendering the procedure more painful for the patient. Further, the placing of the cord is not a procedure which the dentist may delegate to a dental assistant or dental hygienist. Also, the packing of a retraction cord is a most disliked step to in performing a crown or bridge restoration procedure.

Efforts have been made to obviate the noted disadvantages of affecting the retraction of the gingival tissue by the use of a cord. One such known effort is the use of a kaolin clay type material that is mixed with an astringent salt which is simply placed about a prepared tooth to absorb the moisture to cause the gum tissue to shrink. Such a product is marketed by Sybron Dental Specialties under the trademark or brand name ExpaSyl.

It has been noted that such kaolin type material is packaged in a cartridge similar to a typical anesthetic cartridge commonly used in a dental office that requires the cartridge to be used with a syringe. The end of the cartridge is pierced with a needlelike cannula and the force of the syringing pressure is required to extrude the clay like kaolin material through the cannula. Because of the density of the kaolin type material, the cannula requires the opening to be very large so as to enable the kaolin type material to flow therethrough. The large gauge opening of the cannula renders the bending of the cannula difficult and which bending is often required in order to place the material in difficult to reach places within a patient's mouth. Because the opening of the cannula is quite large, difficulty is encountered in placing the kaolin type material about the gingival sulcus in a manner similar to the traditional method of packing cord to retract the gum tissue.

Also, the use of such kaolin type material to retract the gum tissue often results in crumbling of the kaolin material, rendering it difficult to place in the space between the gum tissue and the tooth to attain the desired retraction of the gum tissue. Another noted problem with such kaolin type material is the removal of the kaolin material after the period of time required to affect the hemostatic action or retraction. Generally, the kaolin material is required to be washed out using a water-air spray with extreme care to remove all the kaolin material without restarting any bleeding in the gingival sulcus.

Another known technique for effecting a non-cord retraction and/or hemostatic is disclosed in U.S. Pat. No. 5,676,543. Therein disclosed is a generally two part process utilizing two different viscosities of a silicone material to effect the cordless retraction and/or hemostatic of the gingival sulcus.

Also, U.S. Pat. No. 6,890,177 discloses a more simplified cordless retraction method and device whereby the cordless retraction may be accomplished by resorting to a porous sponge or foam cellular dam which is shaped to conform with the prepared tooth or teeth, arranged to contain a two part silicone type impression material that includes a base portion and a catalyst, whereby the patient's biting force is utilized to apply the necessary pressure to effect the desired retraction.

Other devices and methods are used to retract the gingival sulcus. One product is sold under the trademark Magic Foam-Cord which is dependent upon an expanding vinyl polysiloxane or silicone material which is a two-part, chemically cured component system that are required to be mixed by the dentist at chair side prior to application and which cures or sets to effect the retraction of the gingival tissue.

SUMMARY OF THE INVENTION

The present invention relates to a rolled absorbent compression cap for placement over a tooth to retract the gum or gingiva for forming or enlarging a gingival sulcus around the tooth. A compression cap is formed by rolling an absorbent material such as a paper around a hole or a central bore. The paper is rolled or formed so as to permit the windings to telescope conforming to the shape of the tooth as well as having edges or end portions of the windings applying more direct pressure at the gingival sulcus around the tooth. In one embodiment of the invention, the rolled compression cap may be pre-dosed with an astringent or hemostatic agent. In another embodiment of the invention, the central bore may be filled with a paste or gel material to aid in retraction of the gingiva. Upon applying pressure to the opposing open end of the rolled compression cap may fold inward sealing the opposing open end preventing the paste or gel material from being forced out. In another embodiment the compression cap has an anatomical shape or is scalloped or cut away so as to better fit between adjacent teeth.

It is an object of the present invention to provide a device that can aid in retracting the gum or gingiva tissue forming a gingival sulcus around a tooth needed in a dental procedure easily and with little discomfort to the patient.

It is a further object of the present invention to provide a rolled or telescoping compression cap made from an absorbent material that can wick or soak up fluids from around the tooth in preparation for a dental procedure, such as the taking of an impression.

It is an advantage of the present invention that pressure is more directly applied to the areas where desired to assist in retracting the gingiva aiding in the formation of a gingival sulcus.

It is a further advantage of the present invention that it is relatively easy and inexpensive to manufacture.

It is a feature of the present invention that the compression cap is rolled or is formed by concentric rings or windings so as to permit telescoping of the windings to apply more direct pressure between the gingival and tooth greatly facilitating the formation or widening of a gingival sulcus.

It is another feature of the present invention that it is made of an absorbent material, such as paper.

It is yet another feature of the present invention that it may be pre-dosed with an astringent or hemostatic material.

These and other objects, advantages, and features will become more apparent in view of the following more detailed description.

DETAILED DESCRIPTION OF THE PREFERRED EMBODIMENTS

Figure 1:
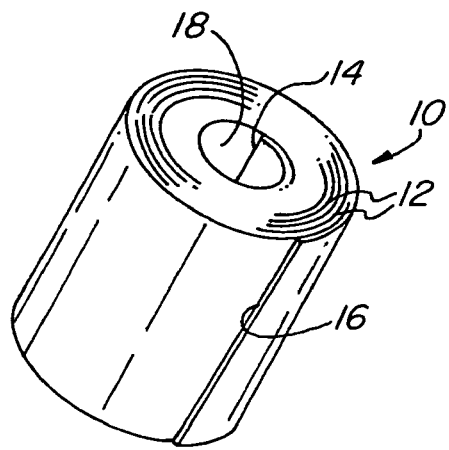
FIG. 1 is a perspective view of an embodiment of the present invention.

FIG. 1 is a perspective view illustrating an embodiment of the present invention. The rolled compression cap 10 is formed by rolling sheet material, such as absorbent paper or cloth or the like, forming wound, spiral, or concentric layers 12. The rolled compression cap 10 has an inner end 14 and an outer end 16. A central bore 18 is formed. The rolled sheet material or paper may be selected so as to have sufficient rigidity to transmit pressure, yet be sufficiently soft or compliant so as not to injure the gingival. The rolled sheet material or paper should also be absorbent so as to absorb fluids from the formed gingival sulcus.

Figure 2:
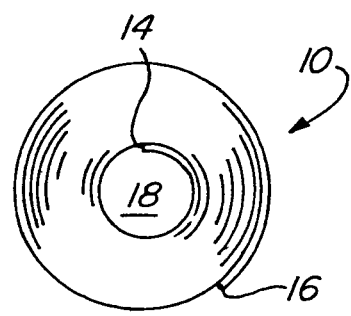
FIG. 2 is a plane view of the embodiment illustrated in FIG. 1.

FIG. 2 is a plan or top view illustrating the rolled compression cap 10 illustrated in FIG. 1. The rolled compression cap 10 is preferable made of an absorbent paper-type material and is rolled around the longitudinal axis of the bore 18. The rolled sheet material forming the layers 12 should be relatively rigid so as to be capable of applying pressure yet sufficiently soft so as to conform to the shape of a tooth. Additionally, the tightness of the winding of the layers 12 should be such that sufficient support is provided to adjacent layers, yet not sufficiently tight so as to prohibit some telescoping or independent extension of adjacent layers 12 so as to conform to a prepared tooth and apply pressure where needed between the tooth and the gingiva for forming or widening a gingival sulcus.

Figure 3:
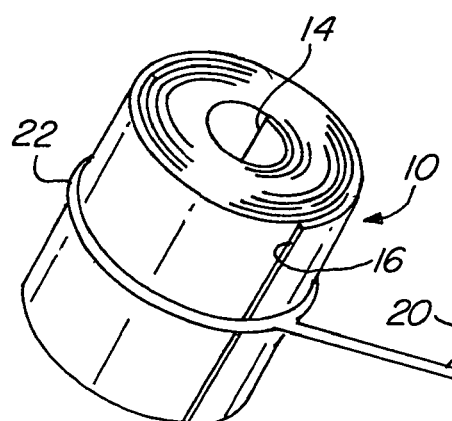
FIG. 3 is a perspective view of another embodiment of the present invention.

FIG. 3 is a perspective view of another embodiment of the present invention illustrating the rolled compression cap 10 having a handle 20 attached to a loop 22. The handle 20 and loop 22 facilitate placement of the relatively small compression cap 10 within a patient's mouth. The loop 22 also aids in preventing the rolled compression cap 10 from unwinding and holds the wound or concentric adjacent layers 12 together. To additionally prevent unwinding, a small amount of adhesive may be placed adjacent the outer end 16 for holding the rolled compression cap 10 together.

Figure 4:
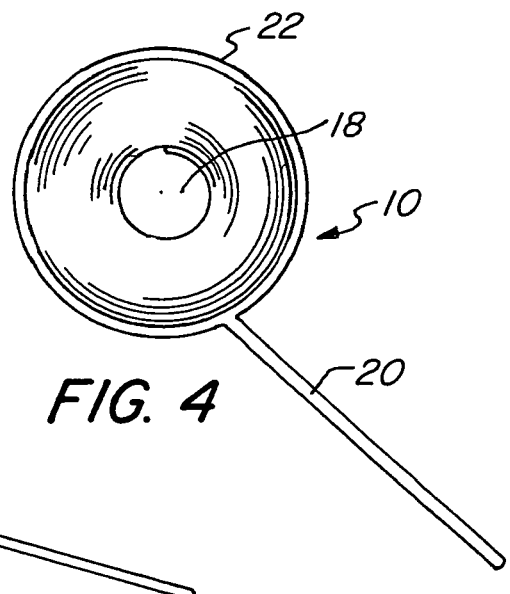
FIG. 4 is a plane view of the embodiment illustrated in FIG. 3.

FIG. 4 is a plan or top view of the rolled compression cap 10 illustrated in FIG. 3. The central bore 18 is clearly illustrated in FIG. 3.

Figure 5:
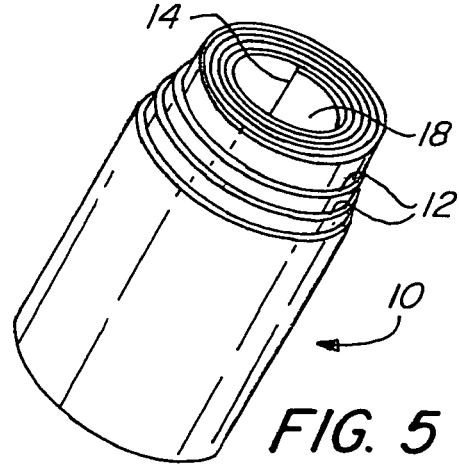
FIG. 5 is a perspective view illustrating the telescoping nature of the windings or concentric cylinders.

FIG. 5 is a perspective view illustrating the rolled compression cap 10 having the layers 12 telescoping or positioned at different heights along the longitudinal axis of the bore 18. The ability of the rolled compression cap 10 to telescope or have the adjacent layers 12 slide along adjacent layers 12 so as to be positioned at different heights greatly facilitates the ability of the different adjacent layers 12 to apply targeted pressure to the gingival sulcus adjacent a tooth for retracting the gingiva or gum tissue.

Figure 6:
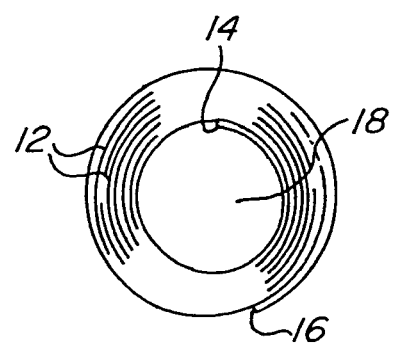
FIG. 6 is a plane view of the embodiment illustrated in FIG. 5.

FIG. 6 is a plan or top view of the embodiment of the rolled compression cap 10 illustrated in FIG. 5. While the rolled compression cap 10 has been illustrated as being formed from a single rolled piece of sheet material, it should be readily apparent that the compression cap may also be made from concentric cylinders having different diameters so as to telescope equivalently or functionally similarly to the rolled or wound embodiment. Additionally, different sizes or diameters of rolled compression caps may be used depending upon the application and size of the tooth or preparation. Similarly, the compression cap may be rolled to form different size or diameter bores depending upon the application and size of the tooth or preparation.

Figure 7:
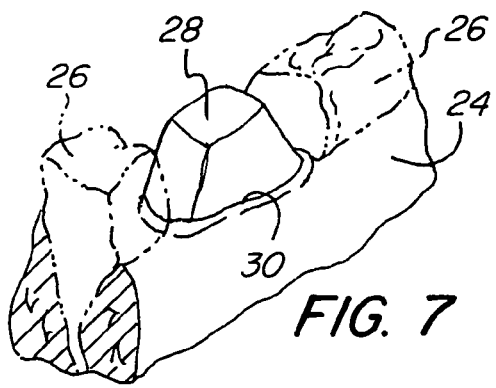
FIG. 7 is a perspective view illustrating a prepared tooth ready for applying the device of the present invention.

FIG. 7 schematically illustrates a portion of a patient's mouth in preparation for a dental procedure illustrating the gum or gingiva 24 and teeth 26 adjacent a prepared tooth 28. Around the prepared tooth 28 is the gingival sulcus which is intended to be retracted or widened. Generally retraction of the gingiva is required in a procedure for placing a cap or crown on the prepared tooth 28. It is often required to separate the gingiva or gum from the prepared tooth 28 to form or widen a gingival sulcus 30 so as to obtain a good impression of the prepared tooth 28. The impression is used in the manufacture of a restoration, such as a crown, a cap, or an inlay to cover the prepared tooth 28.

Figure 8:
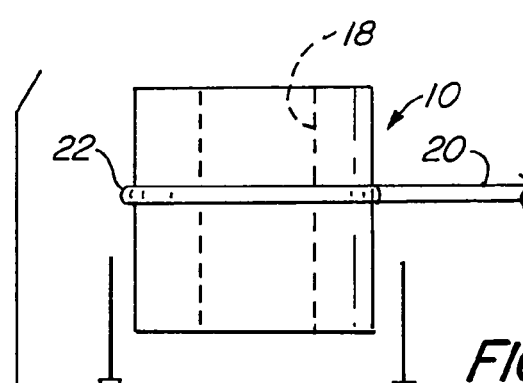
FIG. 8 schematically illustrates the application of the present invention to a prepared tooth.

FIG. 8 illustrates the placement of the rolled compression cap 10 of one embodiment of the present invention over the prepared tooth 28. The loop 22 connected to the handle 20 aids in positioning the rolled compression cap 10 within the relatively tight confines of a patient's mouth. The central bore 18 is positioned over a substantial portion of the prepared tooth 28. However, the ends of the different wound adjacent layers forming the rolled compression cap 10 are substantially positioned over the interface between the prepared tooth 28 and gum or gingiva 24. Some of the adjacent layers or windings are directly positioned within the gingival sulcus 30.

Figure 9:
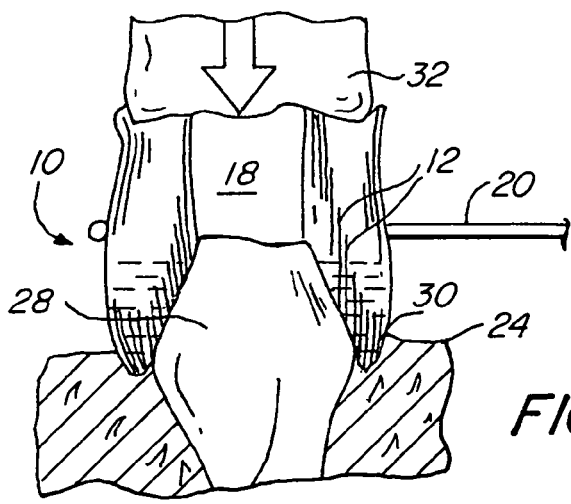
FIG. 9 schematically illustrates the placement of the present invention on a prepared tooth.

FIG. 9 illustrates the rolled compression cap 10 in position on the prepared tooth 28 and the application of downward pressure from an opposing tooth 32. As is clearly illustrated in FIG. 9, the adjacent layers 12 of the rolled compression cap 10 will slide along one another telescoping or moving somewhat to conform to the prepared tooth as well as apply direct mechanical pressure to the gingival sulcus 30 between the prepared tooth 28 and the gum or gingiva 24. This application of precisely targeted mechanical pressure aids in separating or widening the gingival sulcus 30 and gum or gingival 24 away from the surface of the prepared tooth 28. The bore 18 is useful so as to prevent pressure from being applied where it is not needed over the prepared tooth 28. This helps to focus or direct the applied mechanical pressure directly where it is needed within the gingival sulcus 30.

Figure 10:
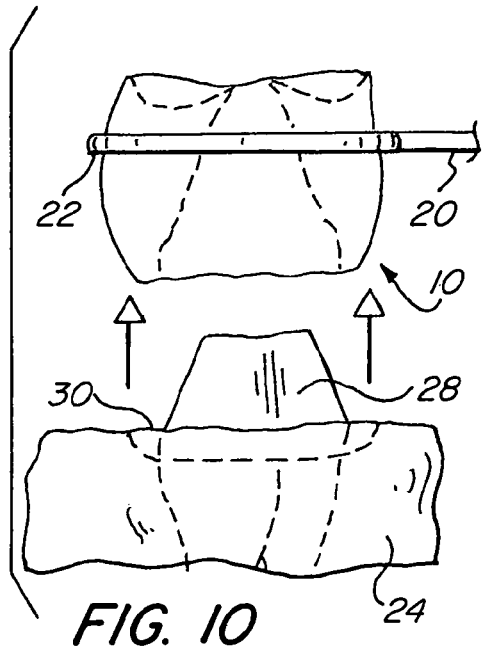
FIG. 10 schematically illustrates removal of the present invention from a prepared tooth.

FIG. 10 illustrates the removal of the rolled compression cap 10 after treatment of the prepared tooth 28 and the gingival 26. The sulcus 30 and gum or gingival are retracted away from the surface of the prepared tooth 28.

Figure 11:
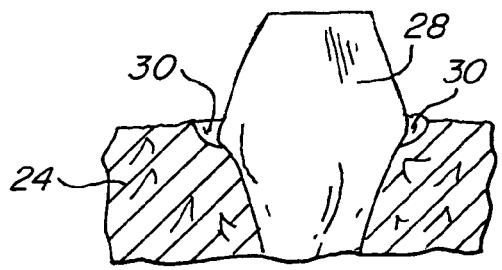
FIG. 11 schematically illustrates the retraction of the gingiva and the formed or widened gingival sulcus after use of the present invention.

FIG. 11 illustrates the prepared tooth 28 and widened gingival sulcus 30 and the gum or gingiva 24 retracted away from the prepared tooth 28 in a condition or state ready to take an impression. The impression is used to make a crown or cap that fits over the prepared tooth 28. A good impression is critical in establishing a tight, secure fit of the cap or crown that is placed over the prepared tooth 28.

Figure 12:
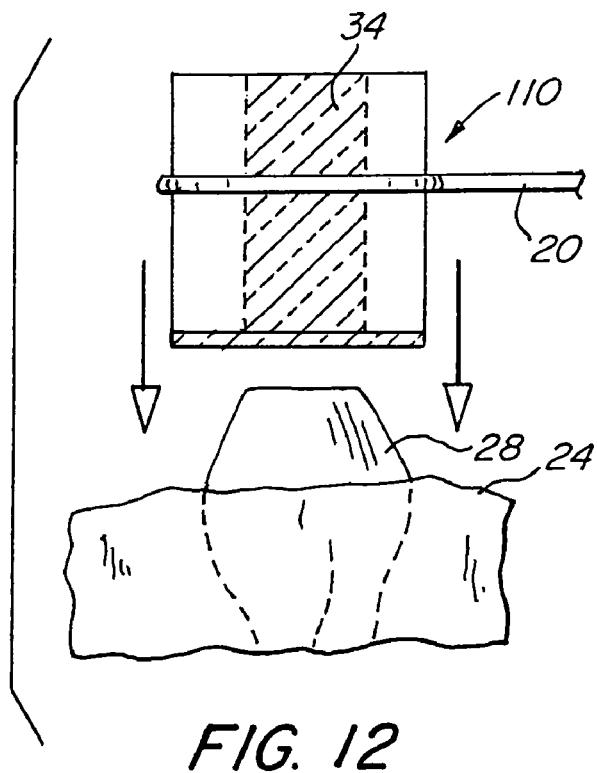
FIG. 12 schematically illustrates the placement of another embodiment of the present invention having a material placed with the bore on a prepared tooth.
Figure 13:
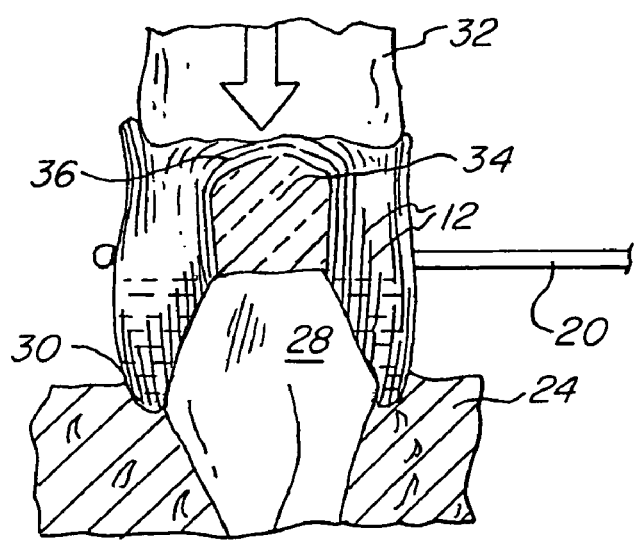
FIG. 13 schematically illustrates the application of the embodiment of the present invention having a material placed with the bore on a prepared tooth.

FIGS. 12 and 13 illustrate another embodiment of the present invention. In this embodiment the rolled compression cap 110 has the central bore 18 filled with a retraction material 34. The retraction material 34 may also extend along an adjacent surface or end of the rolled compression cap 110 to be placed adjacent the prepared tooth 28. This permits a portion of the retraction material 34 to be directly placed adjacent the gum or gingiva and also acts as a path for additional retraction material to migrate along adjacent the surface of the prepared tooth 28 and into the gingival sulcus 30. The retraction material may be in the form of a paste or a gel that contains a chemical agent to facilitate retraction, such as an astringent or hemostatic agent. The material may be a retraction material as disclosed in U.S. Pat. No. 7,241,143 entitled "Pre-loaded Dental Dam and Method for Gingival Tissue Retraction", issuing to Discko, Jr., et al on Jul. 10, 2007, which is herein incorporated by reference. The retraction material 34 may act as a reservoir of retraction material 34 that can migrate between the adjacent layers and surface of the prepared tooth 28 to the gingival sulcus 30. Also, the retraction material 34 can also be absorbed by the adjacent layers 12 and wick down between the surfaces of the prepared tooth 28 to the gingival sulcus 30. As illustrated in FIG. 13 the opposing open end is closed by folded over portions 36 of the adjacent layers 12. The folded over portions 36 help to contain the retraction material 34 and prevent it from being forced out of the opposing open end and also helps to force additional retraction material 34 down the surfaces of the prepared tooth 28 and into the gingival sulcus 30.

Figure 14:
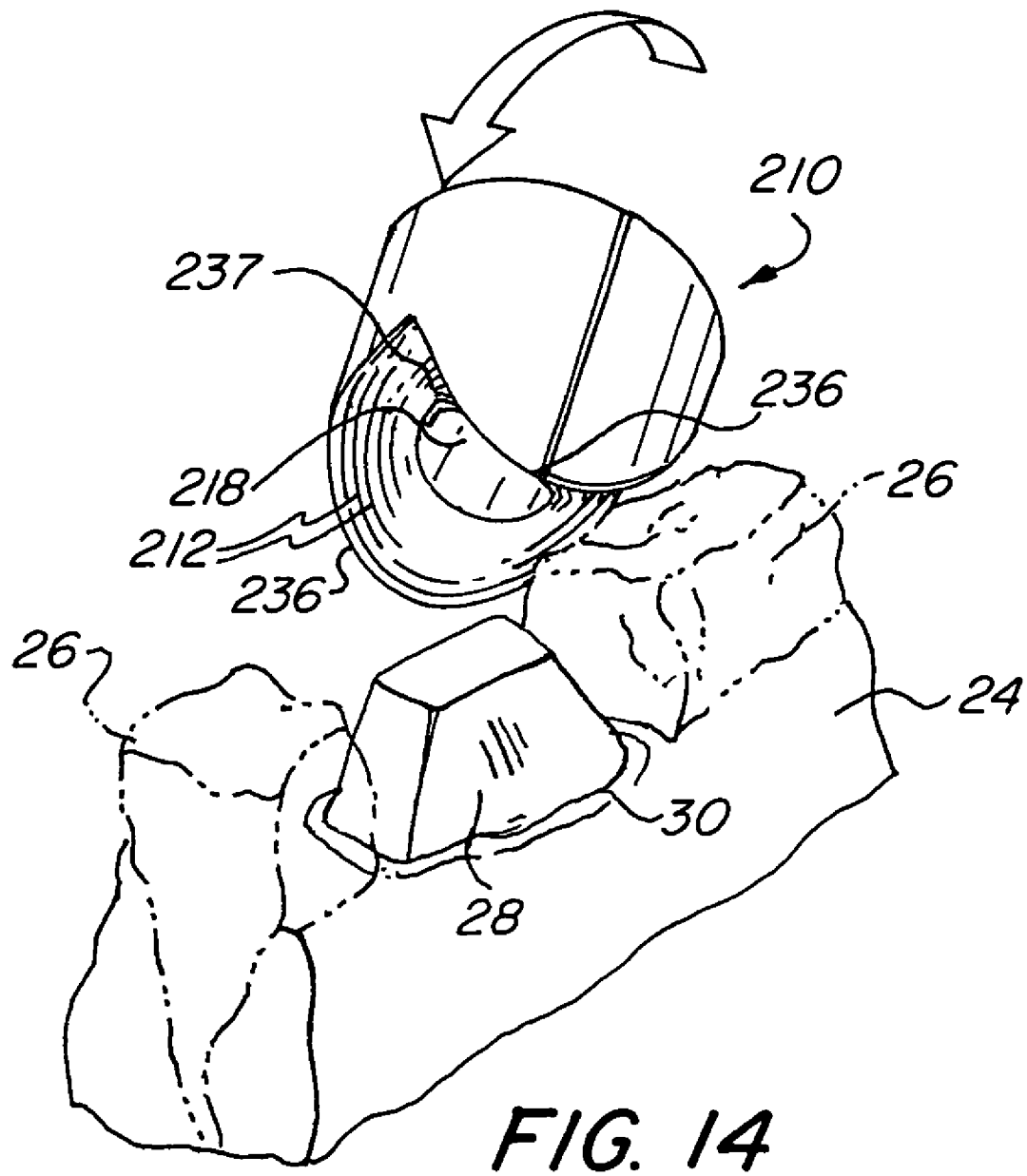
FIG. 14 is a perspective view illustrating the application of another embodiment of present invention having an anatomical or scallop shape placed on a prepared tooth.

FIG. 14 illustrates another embodiment of the present invention having an anatomically or scalloped shaped compression cap 210. The anatomically shaped compression cap 210 has the side surface intended to be placed adjacent the prepared tooth 28 having an anatomical or scalloped shape forming a lower edge 237 on each side that is positioned adjacent teeth 26 and a raised edge 236 that is positioned along the side of the prepared tooth 28 and into the gingival sulcus 30. This anatomical shape aids in accommodating the relatively small space between the prepared tooth 28 and the adjacent teeth 26 and helps to assure that the anatomical rolled compression cap 210 sits snugly over the prepared tooth 28 and is better able to be pressed downward applying targeted mechanical force.

The rolled compression cap as illustrated in the different embodiments makes possible the very targeted and direct application of mechanical force to the gingival sulcus so as to separate the gingiva from the prepared tooth and facilitates retraction. When the patient bites down on the rolled compression cap the center is caused to telescope or collapse somewhat while the outer edges or layers remain relatively rigid. The outer adjacent layers slide and push into the gingival sulcus mechanically facilitating retraction. Additionally, the outer adjacent layers are able to deliver an astringent, hemostatic, or retraction agent directly to the gingival sulcus. The use of absorbent paper material also aids in the wicking or the absorption of fluids, such as saliva and blood, from within the gingival sulcus. This aids in drying the area between the tooth and the gingival sulcus which is necessary for taking a good impression. Depending on the type of paper and the tension of the windings the rolled compression caps can be made to be relatively soft or collapsible or relatively firm providing additional pressure. For example a soft or compliant paper may be used for small delicate locations and a stiffer stronger paper for larger areas, such as around molars or large preparations.

Additionally, an important feature of the rolled compression caps of the present invention is that they may be pre-dosed, soaked, or impregnated with an astringent or hemostatic agent. The astringents that may be used are aluminum chloride, aluminum sulfate, ferric chloride, tannic acid, sodium chloride, kosher salt, aluminum potassium chloride, ammonium potassium chloride, or any astringent that is biocompatible.

A particularly preferred astringent that is relatively mild may be common table salt or sodium chloride, and in particular kosher table salt. The pre-dosed rolled compression caps may be prepared by soaking the absorbent rolled compression cap in a solution of the astringent or hemostatic agent. The solution may be five percent (5%) to fifty percent (50%) by weight of the astringent or hemostatic agent in an appropriate solvent. Preferable the solvent is distilled water. After soaking in the solution, the rolled compression cap may be dried forming the pre-dosed rolled compression cap that contains a dry inactive retraction, astringent, or hemostatic agent. Upon use, the moisture in the patient's mouth activates the retraction, astringent, or hemostatic agent. Additionally, a portion of the retraction material in the core may be absorbed or wicked into the rolled compression cap for easy delivery directly to the gingival sulcus.

Accordingly, the present invention provides a compression cap that conforms to a tooth and gingiva by permitting adjacent layers to move or telescope so as to apply pressure more directly to the gingiva aiding in forming or widening a gingival sulcus. Additionally, a retraction agent or material facilitates the retraction.

While the present invention has been described with respect to several different embodiments, it will be obvious that various modifications may be made without departing from the spirit and scope of this invention.

What is claimed is:

1. A dental retraction compression cap comprising:
a plurality of adjacent layers of absorbent compliant sheet paper material rolled forming a tube comprised of a plurality of adjacent concentric cylinders of different diameters and having a central fixed diameter bore smaller than a lateral dimension of a prepared tooth and adapted to be placed over the prepared tooth, wherein said plurality of adjacent layers have a tightness such that sufficient support is provided to said plurality of adjacent layers and yet permits telescoping of said plurality of adjacent layers so as to apply pressure between the prepared tooth and gingiva,
whereby said plurality of adjacent layers slide axially along each other permitting said plurality of adjacent layers of absorbent compliant sheet paper material to telescope conforming to the shape of the prepared tooth and apply pressure adjacent the prepared tooth aiding in the formation or widening of a gingival sulcus.

2. A dental retraction compression cap as in claim 1 further comprising:
a retraction agent contained within said plurality of adjacent layers.

3. A dental retraction compression cap as in claim 2 wherein:
said retraction agent comprises an astringent.

4. A dental retraction compression cap as in claim 3 wherein:
the astringent comprises sodium chloride.

5. A dental retraction compression cap as in claim 2 wherein:
said retraction agent is selected from the group consisting of aluminum chloride, aluminum sulfate, ferric chloride, tannic acid, kosher salt, aluminum potassium chloride, and ammonium potassium chloride.

6. A dental retraction compression cap as in claim 1 wherein:
said plurality of adjacent layers of absorbent compliant sheet paper material comprise a single rolled sheet of material.

7. A dental retraction compression cap as in claim 1 wherein:
one end of the tube has a scalloped shape, whereby the tube is capable of fitting snugly between adjacent teeth.

8. A dental retraction compression cap comprising:
a plurality of adjacent layers of absorbent compliant sheet paper material forming a tube having a central fixed diameter bore smaller than a lateral dimension of a prepared tooth and adapted to be placed over a the prepared tooth, wherein said plurality of adjacent layers have a tightness such that sufficient support is provided to said plurality of adjacent layers and yet permits telescoping of said plurality of adjacent layers so as to apply pressure between the prepared tooth and gingiva; and
a retraction material placed within the central bore,
whereby said plurality of adjacent layers slide axially along each other permitting said plurality of adjacent layers of absorbent compliant sheet paper material to telescope conforming to the shape of the prepared tooth and apply pressure adjacent the prepared tooth aiding in the formation or widening of a gingival sulcus.

9. A dental retraction compression cap as in claim 8 wherein:
said retraction material extends along an adjacent end of the dental retraction compression cap.

10. A dental retraction compression cap as in claim 8 wherein:
said plurality of adjacent layers of absorbent compliant sheet paper material are adapted to fold over an opposing open end upon application of a longitudinal pressure whereby said retraction material is prevented from being forced out of the opposing open end.

11. A dental retraction compression cap comprising:
a plurality of adjacent layers of absorbent material forming a tube having a central bore adapted to be placed over a prepared tooth, whereby said plurality of adjacent layers slide along each other conforming to the shape of the prepared tooth and apply pressure aiding in the formation or widening of a gingival sulcus;
a loop placed around the tube; and
a handle attached to said loop,
whereby the dental retraction compression cap may be held by said handle and easily positioned over a prepared tooth.

12. A dental retraction compression cap for use in a dental procedure comprising:
a plurality of adjacent layers of absorbent compliant sheet paper material rolled forming a tube comprised of a plurality of adjacent concentric cylinders of different diameters wherein the tube is relatively rigid so as to be capable of applying pressure yet sufficiently soft or compliant to conform to the shape of the tooth and not injure gingiva and having a central fixed diameter bore smaller than a lateral dimension of a prepared tooth and adapted to be placed over the prepared tooth, said plurality of adjacent layers being formed so as to have a tightness such that sufficient support is provided to said adjacent layers and yet permits telescoping of said plurality of adjacent layers so as to apply pressure between the prepared tooth and gingiva and permit said plurality of adjacent layers to axially slide adjacent to one another or telescope upon the application of a longitudinal pressure on one end so as to contact the prepared tooth and gingiva at different heights; and
a retraction agent placed within said plurality of adjacent layers of absorbent material,
whereby said plurality of adjacent layers slide along each other conforming to the shape of the prepared tooth and gingiva and apply pressure adjacent the tooth aiding in the formation or widening of a gingival sulcus.

13. A dental retraction compression cap for use in a dental procedure as in claim 12 wherein:
said retraction agent comprises sodium chloride.

14. A dental retraction compression cap for use in a dental procedure as in claim 12 wherein:
said retraction agent is selected from the group consisting of aluminum chloride, aluminum sulfate, ferric chloride, tannic acid, kosher salt, aluminum potassium chloride, and ammonium potassium chloride.

15. A dental retraction compression cap for use in a dental procedure as in claim 12 wherein:
said plurality of adjacent layers of absorbent compliant sheet paper material comprise a single rolled sheet of material.

16. A dental retraction compression cap for use in a dental procedure as in claim 12 wherein:

one end of the tube has a scalloped shape, whereby the tube is capable of fitting snugly between adjacent teeth.

17. A dental retraction compression cap for use in a dental procedure comprising:
   a plurality of adjacent layers of absorbent compliant sheet paper material forming a tube wherein the tube is relatively rigid so as to be capable of applying pressure yet sufficiently soft or compliant to conform to the shape of the tooth and not injure gingiva and having a fixed diameter central bore smaller than a lateral dimension of a prepared tooth and adapted to be placed over the prepared tooth, wherein said plurality of adjacent layers have a tightness such that sufficient support is provided to said plurality of adjacent layers and yet permits telescoping of said plurality of adjacent layers so as to apply pressure between the prepared tooth and gingiva and said plurality of adjacent layers being formed so as to permit said plurality of adjacent layers to slide adjacent to one another or telescope upon the application of a longitudinal pressure on one end so as to contact the prepared tooth and gingiva at different heights;
   a retraction agent placed within said plurality of adjacent layers of absorbent compliant sheet paper material; and
   a retraction material placed within the central bore,
   whereby said plurality of adjacent layers slide along each other conforming to the shape of the prepared tooth and gingiva and apply pressure adjacent the tooth aiding in the formation or widening of a gingival sulcus.

18. A dental retraction compression cap for use in a dental procedure as in claim 17 wherein:
   said retraction material extends along an adjacent end of the dental retraction compression cap.

19. A dental retraction compression cap for use in a dental procedure as in claim 17 wherein:
   said plurality of adjacent layers of absorbent compliant sheet paper material are adapted to fold over an opposing open end upon application of a pressure whereby said retraction material is prevented from being forced out of the opposing open end.

20. A dental retraction compression cap for use in a dental procedure and widening a gingival sulcus comprising:
   a plurality of adjacent layers of absorbent material forming a tube having a central bore adapted to be placed over a prepared tooth, said plurality of adjacent layers being formed so as to permit said plurality of adjacent layers to slide adjacent to one another or telescope upon the application of a longitudinal pressure on one end so as to contact a tooth and gingiva at different heights;
   a retraction agent placed within said plurality of adjacent layers of absorbent material; and
   a retraction material placed within the central bore,
   a loop placed around the tube; and
   a handle attached to said loop,
   whereby said plurality of adjacent layers slide along each other conforming to the shape of the prepared tooth and gingiva and applying pressure and the retraction agent and material aiding in the formation or widening of the gingival sulcus.

* * * * *